US011085872B2

(12) United States Patent
Dobetti

(10) Patent No.: US 11,085,872 B2
(45) Date of Patent: Aug. 10, 2021

(54) METHOD FOR HAIR ANALYSIS BY POLARIZED LIGHT

(71) Applicant: I LOVE MY BODY RESEARCH S.R.L., Milan (IT)

(72) Inventor: Luca Dobetti, Trieste (IT)

(73) Assignee: I LOVE MY BODY RESEARCH S.R.L., Milan (IT)

(*) Notice: Subject to any disclaimer, the term of this patent is extended or adjusted under 35 U.S.C. 154(b) by 0 days.

(21) Appl. No.: 16/767,388

(22) PCT Filed: Nov. 21, 2018

(86) PCT No.: PCT/EP2018/082012
§ 371 (c)(1),
(2) Date: May 27, 2020

(87) PCT Pub. No.: WO2019/105816
PCT Pub. Date: Jun. 6, 2019

(65) Prior Publication Data
US 2020/0393366 A1    Dec. 17, 2020

(30) Foreign Application Priority Data

Nov. 28, 2017    (EP) .................................. 17204126

(51) Int. Cl.
| | | |
|---|---|---|
| *G01N 21/27* | (2006.01) | |
| *G01N 1/38* | (2006.01) | |
| *G01N 21/25* | (2006.01) | |
| *G01N 33/483* | (2006.01) | |
| *G06K 9/00* | (2006.01) | |
| *G06K 9/20* | (2006.01) | |

(52) U.S. Cl.
CPC ............. *G01N 21/274* (2013.01); *G01N 1/38* (2013.01); *G01N 21/255* (2013.01); *G01N 33/4833* (2013.01); *G06K 9/00134* (2013.01); *G06K 9/2036* (2013.01)

(58) Field of Classification Search
CPC ...... G01N 21/274; G01N 1/38; G01N 21/255; G01N 33/4833; G01N 21/27; G06K 9/00134; G06K 9/2036; G01J 4/04

USPC .................................................. 356/36, 364
See application file for complete search history.

(56) References Cited

U.S. PATENT DOCUMENTS

| | | | |
|---|---|---|---|
| 10,231,531 B2 * | 3/2019 | Witchell | ................ G01N 21/31 |
| 2017/0119130 A1 * | 5/2017 | Witchell | .............. A61B 5/0075 |
| 2017/0164887 A1 * | 6/2017 | Chattopadhyay | .... A42B 3/0433 |

FOREIGN PATENT DOCUMENTS

EP    2518474 A1    10/2012

OTHER PUBLICATIONS

Watts D., Trace Elements and Other Essential Nutrients: Clinical application of tissue mineral analysis, InterClinical Laboratories Educational Publications, 2003; Abstract only.
Underwood E.J. and Suttle N.F., The Mineral Nutrition of Lifestock, 3rd Ed., CAB International, 1999.
Schamberger R.J., Biological Trace Element Research, 87, 1-28, 2002; Abstract only.
Drasch G. and Roider G., Journal of Trace Elements in Medicine and Biology, 16, 27-31, 2002; Abstract only.
Hamilton T. and Schweinsberg E, Versicherungsmedizin, 56, 136-140, 2004; Abstract only.
Seidel S. et al., JAMA, 285, 67-72, 2001; Abstract only.

* cited by examiner

*Primary Examiner* — Roy M Punnoose
(74) *Attorney, Agent, or Firm* — Volpe Koenig

(57) ABSTRACT

A method of hair analysis based on microscope pictures of the hair in polarized light includes a hair conditioning phase performed in a container made of polyethylene or a polymer being in a position lower than polyethylene in the triboelectric series; this is followed by a hair testing phase in which polarized light microscope images of the hair, contacted with a turpentine oil, are taken and further processed using unmixing to obtain information on the amount of analytes present in the hair. Advantageously the present method shows high accuracy even in presence of accidental movements applied to the microscope/sample to be analyzed, such as possibly occurring during daily laboratory practice. Also advantageously, the high accuracy is maintained when different operators are involved in the procedure, being thus substantially unaffected by different ways of manipulating/preparing/photographing the hair sample.

10 Claims, No Drawings

METHOD FOR HAIR ANALYSIS BY POLARIZED LIGHT

FIELD OF INVENTION

The present invention relates to the field of hair analysis from microscope digital pictures of the hair in polarized light.

BACKGROUND OF INVENTION

Hair analysis has been used from many years to assess human systemic level of metal elements. Hair is widely accepted for assessing toxic elements exposure and level of essential metals. The correlation of the analytical data with diseases, metabolic disorders and nutritional status is still object of extensive investigations, aimed to use hair analysis in routine diagnosis, prognosis and therapeutic treatments.

Compared to other types of clinical specimens, hair has different use and even some advantages over blood, urine and saliva. While the latter fluids tend to show current or recent body status, hair represent a longer timeframe strictly related to the long-term metabolism (Watts D., *Trace Elements and Other Essential Nutrients: Clinical application of tissue mineral analysis*, InterClinical Laboratories Educational Publications, 2003).

The same considerations are also valid in veterinary, where mineral concentration in hair is used to assess the mineral status in the animal organism (Underwood E. J. and Suttle N. F., *The Mineral Nutrition of Lifestock*, $3^{rd}$ Ed., CAB International, 1999).

Although hair mineral analysis is routinely carried out by means of a tissue mineral analysis, or thermo-mineralogram analysis (TMA), different investigations have proven that TMA is not a reliable test (Schamberger R. J., *Biological Trace Element Research*, 87, 1-28, 2002; Drasch G. and Roider G., *Journal of Trace Elements in Medicine and Biology*, 16, 27-31, 2002; Hamilton T. and Schweinsberg F., *Versicherungsmedizin*, 56, 136-140, 2004; Seidel S. et al., *JAMA*, 285, 67-72, 2001). TMA is generally not usable for individual diagnostic because of the large number of factors of individual and environmental influences and sources of error of the method of analysis. Moreover, TMA cannot detect organic thermo-volatile or thermo-labile compounds, such as amino-acids, vitamins, hormones, etc., which are present in the hair and have an essential role in the metabolisms and nutritionals.

Alternative methods have been proposed to overcome the limitations given by TMA.

Among them, the patent application EP 2 518 474 discloses a method to determine the chemical composition of the hair by irradiating the hair with polarized light, obtaining a microscope digital pixel-based image (pattern) in refracted polarized light, and elaborating the pattern according to a deconvolution (unmixing) method, whereby the amount of each analyte present in the hair sample is calculated.

The microscope digital pixel-based image, or image pattern of the hair, is the microscope picture of the hair under irradiation and refraction of the polarized light. The image is collected as a digital-based picture, as with the cameras available in commerce (e.g. not possible with the old generation negative tape cameras), being suitably connected to the ocular of the microscope The method allows the determination of a large number of analytes in the hair, such as metals, aminoacids, drugs, hormones, vitamins, pollutants, poisons, etc., thus providing useful information of the physiological and pathological status of the patient and a different "reading" and prospective of the human body functionality beside the standard diagnostics such as blood and urine. The same principles as in EP 2.518.474 are also applied in veterinary for the analysis of animal hair, mainly house pets (dogs, cats) and racing animals (horses).

As taught in EP 2.518.474, deconvolution or unmixing is an algorithm-based process used to reverse the effects of convolution on recorded data. The object of unmixing is to find the solution of a convolution equation of the form:

$$y(\lambda) = \sum_{k=1}^{m} a_k e_k(\lambda) + n(\lambda) \qquad (A)$$

where $y(\lambda)$ represent the recorded signal and is a linear mixing of $e_k(\lambda)$, reference function of the k pure elements or end members, and $a_k$, relative positive weight of each pure elements whose sum must be equal to one.

Unmixing is then the determination of the $a_k$ weights which minimize the E function by means of the ordinary least square statistical method as $$E = \sum_{i=1}^{c} \left| y(\lambda_i) - \sum_{k=1}^{m} \alpha_k e_k(\lambda_i) \right|^2 \qquad (B)$$

knowing the reference function of each pure element $e_k(\lambda)$.

Therefore, the application of the unmixing algorithm determines the relative contribution of each single analyte to the overall digital picture of the hair sample, providing an assessment of the analytes in the hair sample as absolute amount or concentration (ppm, μg/mg, etc.).

The Example 7 of EP 2.518.474 shows the practical application of the method, whereby a single hair is poured onto a glass in the microscope with polarized light, photographed (focused) six times each picture is then elaborated via unmixing. The procedure described in said patent document entails the disadvantage of poor stabilization of the hair to be observed, with the risk that different pictures of the same hair may involve different quality/image resolution, different emitted light patterns, causing a significant variation of assessed analytes amounts. In order to ensure reproducibility, the operator must work very carefully in an air-stable environment, avoid any accidental movement of the microscope or microscope glass, and take repeated pictures as quickly as possible so as to minimize the risk of accidental movement of the sample; however pouring a single hair onto a glass in the microscope, stabilize it and making one or more consecutive pictures of it is a delicate, time demanding operation. External conditions, such as air blow or breath, or careless bumps even if minimal, can move away the hair from a stable position onto the glass substrate, thus needing to restart the operation to get a focused photography; moreover, possible need to remove the glass from the microscope for operative reasons can also result in a substantial movement of the sample from the original position, with the need to restarting the operation anew. A further variable affecting accuracy of the results is the manual capability of different operators to prepare the sample, focus the hair in the microscope for making the picture, etc.

These drawbacks render the procedure described in EP 2.518.474 undesirably time-consuming and with variable levels of accuracy, thus not meeting the commercial demand for fast and reliable hair analysis. Ways to improve the procedure are not evident to find: for example, as shown in the experimental section, the use of common fixative liquids for microscope observations, in case of hair samples exposed to polarized light, failed to improve reproducibility/accuracy of the analysis.

The need remains thus felt and unmet for new procedures capable to improve the accuracy, speed and practicability of hair analysis based on polarized light pictures of the hair.

SUMMARY OF THE INVENTION

The present inventors have now unexpectedly found that the analytical accuracy of a polarized light-based analysis of the hair can be substantially improved if, prior to the microscope testing phase, a conditioning procedure of the hair is performed in a container made of specific polymeric materials, and the testing phase is subsequently performed using a specific fixative liquid. As experimentally found, none of the above two measures is as such effective in improving analytical accuracy; this could only be achieved by combining the two measures, and limitedly to using specific polymeric materials as constituents of the container and specific liquids as carrier system in the testing phase. Based on the above findings, the new method according to the invention is thus essentially characterized by the following steps, synergistically cooperating to enhanced accuracy:

(i) a conditioning phase where the hair sample in stored in a sealed container made of polyethylene or any other polymer being in a position lower than polyethylene in the triboelectric series;

(ii) a testing phase comprising: opening the container and extracting a set of hair; contacting said set of hair with a turpentine oil; taking one or more microscope digital pictures in polarized light of said set of hair and further processing said pictures to obtain the analyte amount information.

Advantageously the high accuracy of the present method was obtained despite movements deliberately applied to the glass support containing the hair: this shows that the new method is substantially "movement-proof", i.e. it ensures a high reproducibility of the analyte determination, even in presence of accidental movements applied to the microscope/sample to be analyzed, such as inadvertently occurring during daily laboratory practice. Also advantageously, such high accuracy was obtained while involving different operators in the procedure, thus showing that the method is substantially unaffected by different ways of manipulating/preparing/photographing the hair sample. A new of polarized light-based hair analysis procedure is thus provided, meeting commercial demands for high accuracy and increased manual practicability

DETAILED DESCRIPTION

The present invention discloses new improved conditions for performing the method of hair analysis described in the patent application EP 2 518 474; according to said application, the chemical composition of the hair is determined by irradiating the hair with polarized light, obtaining a microscope digital pixel-based image (pattern) in refracted polarized light, and elaborating the pattern according to a deconvolution (unmixing) method, whereby the amount of each analyte present in the hair sample is calculated.

Step-wise, the method of EP 2 518 474, comprises:
a) [calibration phase]: constructing a light pattern for each pure analyte (end member);
b) [measuring phase]: constructing a light pattern of the hair sample under analysis;
c) [determination phase] comparing the patterns obtained in a) against the pattern obtained in step b) and determining the relative contribution of each analyte in the hair sample, via software-assisted unmixing processing.

The calibration phase a) needs not be performed every time before analysing a hair sample. It is generally sufficient to perform it once and then use the resulting light patterns of the pure analytes (end members) as references for an unlimited number of hair samples analysis; these will then include steps b) and c) only.

The calibration and measuring phases a) and b) require the same methodology, the difference being in the sample tested, respectively the pure analyte or the hair sample to be analysed. Said methodology requires:

refracting an incident polarized light beam through the analyte/hair sample;

making a microscope digital picture of the analyte/hair sample determining, per each pixel of said digital picture, its wavelength and absorbance;

constructing a spectral pattern (matrix of points) from each digital picture, each point being characterized by the wavelength and absorbance values of a pixel of said picture. For example, a 7 million pixel based digital picture will be transformed in a matrix with 7 million points, each of them characterized by a couple of wavelength and absorbance numbers.

Pixel-based pictures and relative spectral pattern of a thin layer (50 µm) of pure analyte, or the most chemically similar compound (e.g. oxide) if the pure analyte cannot be handled (e.g. sodium, potassium), are used as end member of that pure analyte, being 50 µm the mean diameter of the hair bulb.

The pure analytes (or hair samples) are placed on a microscope glass. The microscope is provided with source of a polarized light which works in the visible range typically at a wavelength from 350 to 800 nm, projecting a beam of polarized light onto the observation glass of the microscope through the sample under observation. To obtain the polarized light, a polychromatic white light is generated by a lamp and polarized by a standard polarizing filter.

A magnification from 5 to 100 times, preferably from 10 to 30 times, is typically used for the observation of the pure analytes and the hair sample. The microscope is also equipped with (or connected to) a digital camera, with a screen capacity of at least seven million pixels to take pictures of the pure analytes and hair samples (bulb area) under observation. The wavelength and transmittance intensity are then determined for each pixel of the picture.

In step c), well-known unmixing algorithms can be used. Examples thereof are the commercial products Unmixing_MCSU, PoissonsNMF, Farsight, Chrysalis, or IDL (Società Italiana degli Autori ed Editori, registration. no. 006091). The unmixing algorithm evaluates the wavelength and absorbance in each pixel and then compares the absorbance of all the pure analytes at that single wavelength value. The unmixing algorithm is applied via a software-assisted processing, which enables reaching the final result in a reasonable amount of time e.g. EP 2 518 474 teaches unmixing is performed only considering the relative weight of the most absorbing analytes at each detected wavelength. A corresponding list of analytes in descending order of absorbance is produced accordingly; within this list, only a fraction of analytes, i.e. those with highest absorbance, are considered for processing by unmixing. In EP 2 518 474, the threshold is typically set at about 15% of the total number of analytes under analysis, since the contribution of absorbance from the other analytes is negligible or zero (e.g. in a list of 70 analytes, only the first 10 are considered for the unmixing processing).

The sample is photographed n times (e.g. 4 to 10), producing n pre-matrixes, whose data are then averaged to construct the actual final matrix.

In the diagnostic test, each hair picture is analyzed in its pixel components, i.e. wavelength and absorbance. The IDL software applies then automatically the unmixing elaboration to the pixel, by selecting among all those end-members (pure analytes) those effectively contributing to the absorbance at that wavelength. The automatic elaboration of all the pixels will provide then the contribution of each end-members and, consequently, the quali-quantitative composition of these analytes in the hair.

The present invention provides a new improved way of performing the afore described method of hair analysis, known as such from patent application EP 2 518 474; in fact the present inventors have surprisingly found that a sustained contact between the hair and certain polymeric materials, within a closed environment and for a sufficient time, is capable to affect the hair structure in such a manner that, after suspension of the same in specific oils, the light pattern emitted by the hair upon exposure to polarized light becomes more constant, i.e. less affected by the particular positioning of the hair on the observation glass and/or its orientation with respect to the source of polarized light. The present improved method thus requires two essential phases i.e.: (i) a conditioning phase, ensuring the contact of the hair with the polymeric material and (ii) an observation phase in which the hair is contacted with/supported by said specific oils.

The conditioning phase (i) is performed prior to phase b) of the method of hair analysis of EP 2 518 474. In said phase (i), the polymeric material making up the container is critical. In fact, only polyethylene or the polymers positioned lower than polyethylene in the triboelectric series (ordered from positively to negatively chargeable materials), were found effective in obtaining, in combination with the present oils, the requested enhancement in reproducibility.

As well known, the triboelectric series ranks polymeric materials in function of their triboelectric effect. The triboelectric effect or triboelectric charging is a type of contact where certain materials become electrically charged after they come into frictional contact with a different material by exchanging electrons between them. Because the electron transfer between different materials is not immediately reversible, the excess electrons in one material remain left behind, while a deficit of electrons occurs in the other one. Thus, a material can develop a positive or negative charge that dissipates after the materials separate. The polarity and strength of the charges produced by friction differ according to the materials. Materials can therefore be listed in order of polarity of the charge separation when they are touched with another object: the triboelectric series. In the triboelectric series, a material towards the bottom of the series will acquire a negative charge when touched to a material higher in the list. The intensity of charging will be higher, larger is the distance of the materials in the triboelectric series. Materials at the bottom of the triboelectric series are called "negative charged" while materials at the top are called "positive charged". An extended discussion of triboelectric properties of polymeric materials, of reference for the present invention, is presented by Z. L. Wang et al. in "Triboelectric Nanogenerators", Springer international Publishing Switzerland, 2016, XXXIII, IBSN 978-3-319-40038-9: pages 10-11 of this publications includes the triboelectric series of materials and polymers ordered according to their chargeability properties, from positive to negative. Based on this series, polymers usable in the frame of the present invention are: polyethylene and those positioned lower to it, like polypropylene, polydiphenyl propane carbonate, polyimide, polyethylene terephthalate, polyvinyl chloride, polytrifluorochloroethylene, polytetrafluoroethylene, etc.

According to conventional terminology, "polyethylene and polymers positioned below it in the triboelectric series" can also be defined as "negatively charged polymers" in the triboelectric series; however, it must be underlined that the "chargeability" underlying the triboelectric effect is that of the polymeric material, not of its constituting molecules, i.e. it does not correlate with the positive or negative charges possibly carried by the polymer at molecular level. Typical example is polyacrylate, which is higher than polyethylene in the triboelectric series, therefore having a weak tendency to be positively charged when frictioned with polyethylene, although its molecule is a polyelectrolyte bearing negative charges.

In accordance with the invention, the expression "polymeric material making up the container" means that the container can be made in-bulk of said material only or, alternatively, said polymeric material accounts for a predominant part of the container, e.g. more than 50%, preferably more than 70%, even more preferably more than 90% by weight of the container; the expression "polymeric material making up the container" also includes the possibility that the polymeric material is layered on the surface of the container, preferably its inner surface: in such cases the said material polymeric will represent a predominant part of the layer, e.g. more than 50%, preferably more than 70%, even more preferably more than 90% by weight of the layer; in such cases the remainder of the container can be indifferently made of any materials, insofar as they are compatible with the layered polymeric material.

The container used in phase (i) is adapted to contain one or more hair, typically a hair sample which may contain a variable number of hair, e.g. from 50 to 200; the container also includes an air-tight sealable opening through which the hair (or hair sample) can be introduced and subsequently extracted. Once in operation, the sealing can be reversible or irreversible: in the first case the same container can be opened/closed more times, allowing repeated storing of different hair samples; alternatively, the sealing can be irreversible, requiring rupture thereof to extract the hair, in which case the container will be disposed after a single use. No specific limitations are present as to the form of the container: this can be a e.g. small bag, envelope, tube, box, were "small" defines to containers suitable to contain 50-200 hair, e.g. with an inner volume of a few mm$^3$, e.g. 1-30 mm$^3$. Proportionally larger containers are usable for proportionally larger hair samples.

The storage time is also important to allow a sufficient conditioning of the hair: the time is typically longer than half a day and is typically comprised between half a day and five days. The storage temperature has also influence and is preferably comprised between 15 and 35° C.; the pressure inside the container is normally the atmospheric one, however storing under vacuum or under pressure in not excluded.

The present phase (ii) represents a new, specific way of performing the phase b) of the hair analysis method of EP 2 518 474. In said phase ii) the supporting liquid used is critical. In fact, among various fixative liquids, only turpentine oils were found to significantly enhance the accuracy of the present method, and only if applied to hair previously stored according to the materials/conditions of step (i). In phase (ii) the container is opened and one or more hair, typically 1-20 hair, e.g. 6-8 hair, are extracted and used for analysis purpose. The hair is then contacted with a suitable amount of a turpentine oil: the turpentine oil can be selected from e.g. tir turpentine (also known as Canada balm) or pinewood turpentine. The contact between hair and oil is preferably effected directly on the microscope glass, on which the two components can be placed in indifferent order; in alternative, the two component are mutually contacted at a different location and then transferred upon the microscope glass by using a standard mean, e.g. a little spoon, pipette, etc. Optionally and where possible, the supporting liquid used in present phase ii) can also be used as supporting liquid in the initial calibration phase of the hair analysis method, in which the light patterns of pure analytes (end members) are construed.

The digital pictures (light patterns) obtained from the present phase ii), and the corresponding light patterns of the pure analytes (end members) obtained in the initial calibration phase are then processed according to phase c) of the hair analysis method of EP 2 518 474, to obtain the actual information on analyte amount.

The parameters and methodology for performing the polarized light analysis and the analyte determination are well-known in the art. Specifically, the digital pictures (light patterns) of the hair are processed via software-assisted unmixing as described e.g. in EP 2 518 474, determining the relative contribution of each analyte present in the hair sample; the light patterns are typically a matrix of points corresponding to the number of pixels of the photographic image of the hair. Further details of the method are described in EP 2 518 474, herein incorporated by reference.

The present method has no particular limitation as to the type and number of analytes which can be determined. It allows the quantification of analytes in the hair, such as metals, aminoacids, drugs, hormones, vitamins, pollutants, poisons, etc., thus providing useful information of the physiological and pathological status of the patient and a different "reading" and prospective of the human body functionality beside the standard diagnostics such as blood and urine. Example of testable analytes are:

metals like e.g.: silver, calcium, cobalt, chrome, iron, lithium, magnesium, manganese, molybdenum, cadmium, potassium, selenium, sodium, strontium, copper, tin, vanadium, zinc, aluminum, arsenic, barium, cadmium, mercury, nickel, lead, uranium, etc.;
  non-metal elements like e.g.: phosphorus, fluorine, iodine, silica, sulfur, etc.;
  amino-acids like e.g. aspartic acid, glutamic acid, alanine, arginine, cysteine, phenylalanine, glycine, isoleucine, hystidine, leucine, lysine, methionine, proline, serine, taurine, tyrosine, threonine, tryptophan, valine, and derivatives thereof;
  vitamins like e.g. folic acid, niacin, vitamin A, vitamin B1, vitamin B2, vitamin B5 or pantothenic acid, vitamin B6, vitamin B12, vitamin C, vitamin D, vitamin E, vitamin H or biotin, vitamin K, and derivatives thereof;
  hormones like e.g. estrogen, progesterone, oxytocin, dopamine, serotonin, noradrenalin, adrenalin, testosterone, etc., and derivatives thereof.

Examples of preferred analytes are alkaline or earth alkaline metals, in particular potassium, lithium, magnesium.

The invention is now described by reference to the following non-limiting examples.

Experimental Part

The authors have tested different liquids (see Table 1), either commonly used in the sample preparation for microscope examination or possessing optimal optical characteristics, namely a refractive index similar to that of the glass (n=1,53-1,55) used in microscopy. The aim of the authors was to select the most suitable liquid(s) for the analysis in polarized light object of EP 2.518.474.

TABLE 1

List of the supporting liquids tested.

| Liquid | Refractive Index | Viscosity (cP) |
|---|---|---|
| Water | 1.33 | 0.9 |
| Ethanol | 1.36 | 1.1 |
| Carbon tetrachloride | 1.46 | 0.9 |
| Toluene | 1.50 | 0.6 |
| Methyl salicylate | 1.54 | n.a. |
| Ethyl salicylate | 1.52 | n.a. |
| Ethylene glycol | 1.43 | 16 |
| Glycerol | 1.47 | 950 |
| Furan | 1.52 | 1.5 |
| Glucose solution 75% | 1.48 | 1.400 |
| Canada balsam (fir turpentine) | 1.52 | n.a. |
| Turpentine (pinewood) | 1.47 | 1.375 |
| Parafin, liquid | 1.48 | 80 |
| Cedar oil | 1.52 | 985 |
| Castor oil | 1.48 | 650 |
| Entellan ™ | 1.50 | n.a. |
| Neo-Mount ™ | 1.46 | n.a. |
| DPX Mountant | 1.52 | 600-700 |

The authors have spread the liquid on the microscope glass, sunk the hair in the liquid for analysis and photographed by different operators as in the Example 7 of EP 2.518.474. The relative standard deviation (RSD) was thus determined, especially that of the most critical analytes which have shown the highest RSD, such as lithium, potassium, magnesium.

The authors have also tested further parameters to check carefully the accuracy of the measurement taking into account the operational steps from sampling to make pictures of the hair. These steps include sampling 50-100 hair in a sampling centre, pouring them in a small bag or container, sending them to a laboratory, preparing them on the microscope glass with a stabilizing liquid and making their pixel-based pictures in polarized light. The pictures are then elaborated by unmixing as previously described for the quantification of the analytes.

TABLE 2

List of the materials tested.

Polystyrene
Rubber
Brass
Paper
Wax paper
Leather
Cellulose acetate (rayon)
Polyester
Polyacrylate
Polyamide (nylon)
Silk TABLE 2-continued List of the materials tested.

Aluminum
Polyethylene
Polypropylene
Polyvinylchloride
Teflon

Example 1

About 50-100 hair are sampled from the latero-parietal area of the head of a volunteer and pooled together. One hair taken from the pool is immersed by the first operator (A) in a supporting liquid as in Table 1, which was previously spread onto a microscope glass. The glass is then placed in a microscope (Olympus BH2) equipped with a polarizing filter (Nikon). Eight digital pictures of refracted polarized light are made using a digital camera (Nikon D70S). After each photography, the glass is removed and placed again in the microscope. The analytes are evaluated by means of the unmixing algorithm-based process as in EP 2.518.474.

The successive operator (B) then removes the hair from the glass and repeats the same operations as above using the same supporting liquid and glass. Analogously, the same operations are carried out one by one by the successive operators (C to F).

A second hair is taken out from the pool for testing with a second liquid by the six operators as above. The entire procedure is iteratively carried out by taking out a new hair from the pool, which is tested with a different supporting liquid.

The entire procedure is further repeated on a hair sample without using a supporting liquid and the obtained results are taken as a reference.

The relative standard deviation (RSD) of the three most critical elements (lithium, potassium and magnesium) is determined for each liquid used as a support, by means of $$RSD = (SD/Mean) * 100$$

where
SD is the standard deviation of each tested element (lithium, potassium and magnesium) from 6 measurements of the same hair, and
Mean is the mean values of each tested element (lithium, potassium and magnesium) from 6 measurements of the same hair.

The results (Table 3) show a comparable RSD for all the different supporting liquid tested. Only turpentine oils show a slightly lower RSD versus reference, but without a clear statistical meaning. Therefore, this finding must be only taken as a qualitative observation.

TABLE 3

| Liquid | RSD (%) | | |
|---|---|---|---|
| | Li | K | Mg |
| REFERENCE (no liquid - air) | 11.7 | 10.9 | 14.1 |
| Water | 12.0 | 11.0 | 14.0 |
| Ethanol | 12.7 | 12.0 | 14.4 |
| Carbon tetrachloride | 12.3 | 12.1 | 14.0 |
| Toluene | 12.5 | 11.9 | 14.2 |
| Methyl salicylate | 11.9 | 10.5 | 13.8 |
| Ethyl salicylate | 11.4 | 10.9 | 14.1 |
| Ethylene glycol | 11.5 | 11.0 | 13.8 |
| Glycerol | 12.0 | 10.8 | 14.5 |
| Furan | 12.5 | 12.0 | 14.8 |
| Glucose solution 75% | 11.9 | 10.8 | 14.4 |
| Canada balsam (fir turpentine) | 10.4 | 10.0 | 12.7 |
| Turpentine (pinewood) | 10.3 | 9.8 | 12.9 |
| Parafin, liquid | 12.4 | 11.1 | 13.7 |
| Cedar oil | 11.9 | 10.9 | 13.8 |
| Castor oil | 12.4 | 11.4 | 13.4 |
| Entellan ™ | 13.0 | 10.8 | 14.0 |
| Neo-Mount ™ | 12.0 | 11.2 | 14.0 |
| DPX Mountant | 11.8 | 11.0 | 14.3 |

Example 2

About 50-100 hair are sampled from the latero-parietal area of the head of a volunteer and pooled together. The hair sample is split and poured in small bags (pouches) made of different materials. All bags are sealed and stored at temperature of about 20-30° C. for a period of one day. At the end of the conditioning period, the bags are opened and a single hair is taken from each of them for microscope analysis.

The hair, without any supporting liquid, is then poured onto a microscope glass, which is then placed in a microscope (Olympus BH2) equipped with a polarizing filter (Nikon). Eight digital pictures of refracted polarized light are made using a digital camera (Nikon D70S). After each photography, the glass is gently removed and placed again in the microscope. The analytes are evaluated by means of the unmixing algorithm-based process as in EP 2.518.474.

The successive operator (B) then removes the hair from the glass and repeats the same operations as above using the same glass. Analogously, the same operations are carried out one by one by the successive operators (C to F).

The above procedure is then iteratively carried out by sampling new hair and using different bag (container) materials.

The relative standard deviation (RSD) of the three most critical elements (lithium, potassium and magnesium) is determined for each material.

The results (Table 4) did not show any statistically meaningful difference of RSD for all the different materials tested.

TABLE 4

| Material | RSD (%) | | |
|---|---|---|---|
| | Li | K | Mg |
| Polystyrene | 12.4 | 11.7 | 14.4 |
| Rubber | 12.0 | 11.7 | 14.9 |
| Brass | 13.0 | 12.0 | 15.2 |
| Paper | 12.5 | 12.0 | 15.0 |
| Wax paper | 12.6 | 11.4 | 14.0 |
| Leather | 12.8 | 11.5 | 14.9 |
| Cellulose acetate (rayon) | 11.9 | 11.4 | 14.1 |
| Polyester | 12.5 | 11.9 | 13.9 |
| Polyacrylate | 12.5 | 12.8 | 14.1 |
| Polyamide (nylon) | 12.4 | 12.5 | 14.1 |
| Silk | 12.0 | 12.8 | 14.8 |
| Aluminum | 12.4 | 11.9 | 14.0 |
| Polyethylene | 13.3 | 11.8 | 13.9 |
| Polypropylene | 12.9 | 12.4 | 13.9 |
| Polyvinylchloride | 11.9 | 10.8 | 13.8 |
| Teflon | 12.7 | 11.7 | 14.3 |

Example 3

About 100-200 hair are sampled from the latero-parietal area of the head of a volunteer and pooled together. The hair are poured in a small bag (pouch) made of the following materials: paper, rayon, nylon, aluminum (Al), polyethylene (PE), polypropylene (PP) and polyvinylchloride (PVC). All bags are sealed and stored at temperature of 20-30° C. for a period of one day. At the end of the conditioning period, the bags are opened and a single hair is taken from each of them for microscope analysis.

The hair from a first bag is immersed by the first operator (A) in a supporting liquid. The glass is then placed in a microscope (Olympus BH2) equipped with a polarizing filter (Nikon). Eight digital pictures of refracted polarized light are made using a digital camera (Nikon D70S). After each photography, the glass is removed and placed again in the microscope. The analytes are evaluated by means of the unmixing algorithm-based process as in EP 2.518.474.

The successive operator (B) then removes the hair from the glass and repeats the same operations as above using the same supporting liquid and glass. Analogously, the same operations are carried out one by one by the successive operators (C to F).

A second hair is taken out from the same pool for testing with a second supporting liquid by the six operators as above. The entire procedure is iteratively carried out by taking out a new hair from the pool, which is tested with a different supporting liquid. The supporting liquids are castor oil, glycerol, ethylene glycol, DPX-Mountant, Neo-Mount™, fir turpentine (Canada balsam) and pinewood turpentine.

The same operations as above are repeated using hair taken from different small bags.

The relative standard deviation (RSD) of the three most critical elements (lithium, potassium and magnesium) is determined for each liquid used as a support.

The results (Table 5) show clearly that the combination of PE, PP and PVC with turpentine oils performs much better than the other combination tested. The relative standard deviation of the combination of PE, PP and PVC with turpentine oils is markedly lower than those of the other ones.

TABLE 5

RSD (%) of the different combination between bag materials and supporting liquids.

| | | Castor oil | Glycerol | Ethylene Glycol | DPX Mountant | Neo-Mount ™ | Fir turpentine Canada balsam | Pinewood turpentine |
|---|---|---|---|---|---|---|---|---|
| Paper | Li | 12.0 | 11.4 | 12.1 | 13.0 | 11.9 | 11.0 | 10.8 |
| | K | 11.3 | 10.7 | 11.9 | 11.7 | 11.0 | 11.2 | 10.8 |
| | Mg | 14.1 | 14.4 | 14.4 | 14.0 | 14.4 | 13.0 | 11.6 |
| Rayon | Li | 11.7 | 11.8 | 11.7 | 12.3 | 11.9 | 10.2 | 10.9 |
| | K | 11.5 | 12.0 | 11.4 | 12.1 | 12.0 | 10.7 | 10.8 |
| | Mg | 14.3 | 14.0 | 14.1 | 15.0 | 14,7 | 12.0 | 12.9 |
| Nylon | Li | 12.5 | 12.6 | 12.0 | 12.8 | 12.5 | 11.7 | 11.2 |
| | K | 12.0 | 12.0 | 12.3 | 11.5 | 11.6 | 11.2 | 11.3 |
| | Mg | 14.4 | 13.0 | 13.9 | 13.9 | 13.7 | 12.0 | 11.9 |
| Al | Li | 11.8 | 12.0 | 11.5 | 12.5 | 12.0 | 10.8 | 10.8 |
| | K | 11.0 | 11.3 | 10.8 | 11.7 | 11.5 | 10.3 | 10.5 |
| | Mg | 13.6 | 13.1 | 14.9 | 13.6 | 14.1 | 12.7 | 11.9 |
| PE | Li | 12.5 | 12.4 | 12.4 | 12.9 | 12.1 | 7.0 | 6.9 |
| | K | 11.7 | 12.0 | 11.8 | 12.0 | 12.1 | 6.7 | 6.3 |
| | Mg | 14.4 | 13.8 | 14.7 | 15.0 | 14.8 | 8.5 | 8.8 |
| PP | Li | 12.8 | 12.0 | 12.8 | 12.4 | 12.5 | 7.5 | 7.6 |
| | K | 12.3 | 11.8 | 11.9 | 11.7 | 11.8 | 6.6 | 7.0 |
| | Mg | 13.3 | 13.9 | 15.1 | 14.4 | 14.7 | 8.4 | 7.9 |
| PVC | Li | 12.4 | 12.4 | 12.5 | 12.8 | 12.6 | 7.1 | 7.4 |
| | K | 11.7 | 11.5 | 11.0 | 12.0 | 11.9 | 6.4 | 6.1 |
| | Mg | 13.9 | 14.5 | 15.1 | 15.0 | 14.4 | 8.0 | 8.2 |

The invention claimed is:

1. A method to analyze hair composition, based on processing light patterns obtained from a microscope digital picture in polarized light of a hair sample, wherein the amount of each analyte present in the hair sample is calculated via unmixing, the method comprising
   a) a calibration phase, wherein the light patterns of pure analytes are constructed taking one or more microscope digital pictures in polarized light of said pure analytes;
   b) a measuring phase, wherein the light pattern of the hair sample is constructed taking one or more microscope digital pictures in polarized light of said hair sample; each of said light patterns being a construction of a spectral pattern from microscope digital picture, wherein each point (pixel) of the picture is characterized by its wavelength and absorbance;
   c) a determination phase, wherein the light patterns of a) and b) are compared and elaborated via software-assisted unmixing, thereby determining the relative contribution of each analyte present in the hair sample, and therefrom its absolute amount or concentration, wherein
prior to said measuring phase b) a conditioning phase is performed, comprising storing the hair sample, during a period of time of at least half a day, in a sealed container made of a polyethylene or a polymer being in a position lower than polyethylene in the triboelectric series; then opening said container, extracting a set of hair and contacting said set of hair with a turpentine oil.

2. The method according to claim 1, wherein said polymer being in a position lower than polyethylene in the triboelectric series is chosen from the group consisting of: polypropylene, polydiphenyl propane carbonate, polyimide, polyethylene terephthalate, polyvinyl chloride, polytrifluorochloroethylene, and polytetrafluoroethylene.

3. The method according to claim 1, wherein said turpentine oil is fir turpentine or pinewood turpentine.

4. The method according to claim 1, wherein said conditioning phase has a duration of from one to five days.

5. Method The method according to claims 1 4, claim 1 wherein said conditioning phase is performed at a temperature between 15 and 35° C.

6. The method according to claim 1, wherein said container is a small-volume envelope, bag, tube or box.

7. The method according to claim 1, wherein set of hair consists of 1 to 20 hairs.

8. The method according to claim 1, further comprising having an accuracy, expressed as relative standard deviation of at least 6 measures of the same set of hair, ranging from 5 to 20%, preferably from 8 to 18%.

9. The method according to claim 1, wherein said analytes include metals, amino-acids, drugs, hormones, vitamins, pollutants, poisons.

10. The method according to claim 9, wherein said metals include alkaline or earth-alkaline metals.

\* \* \* \* \*